(12) United States Patent
Baumann et al.

(10) Patent No.: US 10,342,449 B2
(45) Date of Patent: Jul. 9, 2019

(54) ELECTROCARDIOGRAM DEVICE AND METHODS

(71) Applicants: Eric Baumann, San Diego, CA (US); Lev Korzinov, San Diego, CA (US); David Churchville, San Diego, CA (US)

(72) Inventors: Eric Baumann, San Diego, CA (US); Lev Korzinov, San Diego, CA (US); David Churchville, San Diego, CA (US)

(73) Assignee: Ventrilink Corporation, San Diego, CA (US)

( * ) Notice: Subject to any disclaimer, the term of this patent is extended or adjusted under 35 U.S.C. 154(b) by 0 days.

(21) Appl. No.: 16/114,519

(22) Filed: Aug. 28, 2018

(65) Prior Publication Data

US 2019/0008406 A1 Jan. 10, 2019

Related U.S. Application Data

(62) Division of application No. 15/252,154, filed on Aug. 30, 2016.

(60) Provisional application No. 62/211,928, filed on Aug. 31, 2015.

(51) Int. Cl.
| | |
|---|---|
| *A61B 5/04* | (2006.01) |
| *A61B 5/046* | (2006.01) |
| *A61B 5/00* | (2006.01) |
| *A61B 5/0456* | (2006.01) |
| *A61B 5/0464* | (2006.01) |
| *A61B 5/0476* | (2006.01) |
| *A61B 5/113* | (2006.01) |

(52) U.S. Cl.
CPC ............ *A61B 5/046* (2013.01); *A61B 5/0022* (2013.01); *A61B 5/0456* (2013.01); *A61B 5/0464* (2013.01); *A61B 5/7246* (2013.01); *A61B 5/7282* (2013.01); *A61B 5/742* (2013.01); *A61B 5/746* (2013.01); *A61B 5/0476* (2013.01); *A61B 5/113* (2013.01)

(58) Field of Classification Search
CPC ..... A61B 5/046; A61B 5/0464; A61B 5/7282; A61B 5/742; A61B 5/746; A61B 5/0456; A61B 5/7246; A61B 5/0022; A61B 5/113; A61B 5/0476
See application file for complete search history.

(56) References Cited

U.S. PATENT DOCUMENTS

| | | |
|---|---|---|
| 5,704,365 A | 1/1998 | Albrecht et al. |
| 5,819,007 A | 10/1998 | Elghazzawi |
| 6,016,442 A | 1/2000 | Hsu et al. |
| 6,418,340 B1 | 7/2002 | Conley et al. |
| 6,463,320 B1 | 10/2002 | Xue et al. |
| 7,058,444 B2 | 6/2006 | Logan et al. |

(Continued)

*Primary Examiner* — Rex R Holmes
(74) *Attorney, Agent, or Firm* — Mark Wisnosky

(57) ABSTRACT

Devices and methods are described that provide improved diagnosis from the processing of physiological data. The methods include use of multiple algorithms and intelligently combing the results of multiple algorithms to provide a single optimized diagnostic result. The algorithms are adaptive and may be customized for particular data sets or for particular patients. Examples are shown with applications to electrocardiogram data, but the methods taught are applicable to many types of physiological data.

8 Claims, 12 Drawing Sheets

(56) References Cited

U.S. PATENT DOCUMENTS

| | | |
|---|---|---|
| 7,142,907 B2 | 11/2006 | Xue et al. |
| 7,263,399 B2 | 8/2007 | Carlson |
| 8,433,399 B1 | 4/2013 | Nosrati et al. |
| 8,478,389 B1 | 7/2013 | Brockway et al. |
| 2006/0264769 A1 | 11/2006 | Satin et al. |
| 2011/0166468 A1 | 7/2011 | Prystowsky et al. |
| 2013/0184600 A1 | 7/2013 | Tan et al. |
| 2014/0031952 A1 | 1/2014 | Harshbarger et al. |
| 2015/0199010 A1* | 7/2015 | Coleman .............. A61B 5/0006 345/156 |
| 2016/0000349 A1 | 1/2016 | Sullivan et al. |

* cited by examiner

ELECTROCARDIOGRAM DEVICE AND METHODS

CROSS-REFERENCE TO RELATED APPLICATIONS

This application claims priority to U.S. Provisional patent application 62/211,928, titled Electrocardiogram Device and Methods, filed 31 Aug. 2015, and is a divisional of U.S. non-provisional application Ser. No. 15/252,154, titled Electrocardiogram Device and Methods, filed 30 Aug. 2016, currently pending, both having common inventors.

BACKGROUND OF THE INVENTION

Technical Field

The present invention relates to a health care device including physiological data acquisition and methods of analysis and use for the device.

Related Background Art

As sensors for physiological data and data acquisition and data handling systems have improved, the amount of physiological data available to caregivers has expanded. It is now common practice to acquire data continuously from electronic sensors attached to patients. Nonlimiting examples of such sensors include temperature probes, probes sensitive to movement to detect breathing, sensors that detect electrical signals from the patient such as electroencephalograms (EEG) and electrocardiograms, sensors for chemistry such as blood oxygen detectors and blood glucose levels. The data is typically acquired versus time. The signal from the sensors is often a voltage or current measurement that is passed through an analog to digital converter to provide a numeric intensity measurement versus time. The analyses look for variations or patterns in the acquired data that are indicative of a disease or abnormal state. In many cases, such as that in the case of electroencephalogram and electrocardiogram data, the data represents repeating waveform patterns. The analysis uses filtering and transform techniques to extract waveform morphology, fundamental frequencies and patterns in the acquired data. The data may be acquired over periods of time from seconds to months. The sensors and data acquisition may be used for patients that are not moving, such as those confined to a bed and those in an intensive care unit of a hospital or the sensors may be attached to ambulatory patients and data is collected continuously as the patient moves about in their normal life routines.

A common feature of the data analysis for such physiological information is to look for anomalies that may have indicated either a disease state or a critical state where a caregiver intervention is required to aid the patient. The latter are common in intensive care unit situations. The large amount of data being acquired from a large number of patients has required the development of automated routines to evaluate the collected data. Frequently the analysis is used to provide automated response, such as in the case of insulin dosing systems responsive to automated blood glucose measurements or in the case f pace makers where an external electrical stimulus is provided upon detection of irregularity in the patient's heartbeat. The physiological data analysis is also frequently used to trigger alarms indicating immediate action is required, such as in an intensive care unit monitoring of an at risk patient. A common failure of all of these analyses and is that false alarms are common. It has been reported that in electrocardiogram data collected in an intensive care unit as much as 86% of the alarms were false alarms.

The data analysis typically involves looking for patterns in the data that are indicative of a disease or abnormal state. Automated algorithms are applied to measure for example in the case of an electrocardiogram, the heart rate, variations in the heart rate and shapes of the repeating waveforms. Algorithms are typically tested against a standard database of acquired data that includes cases where diagnoses of the state of the patients have been independently confirmed. Heretofore algorithms have been tested one at a time and optimized for accuracy and sensitivity to a particular condition. The goal has been to find a single algorithm that will provide the sensitivity and accuracy for all patients. No such algorithm has been found and indeed variations in patients and conditions make such a Holy Grail algorithm unlikely. Caution has dictated to set the sensitivity of the algorithm to be at a very high value, so as to not miss disease or emergency states. This procedure has resulted in algorithms that when applied to the general population of patients, results in errors especially in the form of excessive false positive results for disease or emergency responses. Algorithms optimized for a database have been found on average when applied to individual patients to produce excessive errors that must be reconciled by a trained technician.

The current state of the art for detecting cardiac events in ambulatory patients involves either running a single algorithm on a patient attached device or running a single algorithm on servers that receive a full disclosure data stream from an ambulatory patient attached device. In some cases, a technician reviews every beat of one or two days of full disclosure ECG using a semi-automated algorithm that assists the technician in this review. Electrocardiogram data acquired over a period of days is typically referred to as a "Holter scan" and provides detailed information on the actual number of beats of each morphology, number of abnormal beats, and exact length and type of arrhythmic episodes. Ambulatory algorithms are typically tuned on a small data set to be as sensitive as practical on the entire patient population, and these performance numbers are published using a specific standard so that physicians can compare the performance of different algorithms on a standard small data sent constructed to reflect what the algorithm would encounter in the real world. This usually results in a large number of false positive events that a technician must deal with in order to get to acceptable levels of sensitivity. These false positive events require technician time to review and increase the cost of providing ambulatory monitoring services. In addition, device side algorithms or server side algorithms typically do not provide quantifiable beat counts as a Holter scan would. They also do not typically provide interpretive statements, which the technician applies after reviewing and possibly correcting the event presented by the algorithm.

Patients may also present with distinctly different cardiac signals depending on their disease state, the normal amplitude of the electrical activity of their heart, the orientation of their heart in their chest cavity and other idiosyncrasies provide challenges to detecting events with high specificity. Currently, a single algorithm must take into account all of the possible signals it may encounter from any patient in order for the algorithm to provide adequate sensitivity and diagnostic yield. This generally results in large numbers of false positive, and typical efforts to reduce the number of false positives (increase specificity) usually result in some loss of sensitivity—i.e. the algorithm could miss real events.

Improved methods that maintain the sensitivity while reducing false positive results are needed. The discussions here will demonstrate the techniques applied specifically to electrocardiogram data, but those skilled in the art will readily see the applicability to any other similar timing varying physiological data.

DISCLOSURE OF THE INVENTION

The present invention solves the challenges and increases specificity of a single algorithm approach by running multiple algorithms on a full disclosure electrocardiogram data stream and combining multiple approaches to provide improved diagnoses. In one embodiment the invention includes automatically determining a best algorithm personalized to a particular patient. In another embodiment technician feedback on initial data is used to select a preferred algorithm to be used in subsequent event detection for the particular patient. In another embodiment the invention involves running a Holter scan for a first time period of full disclosure ECG from a patient and incorporating that feedback to be used by the algorithm for event detection for subsequent time periods over a typical ambulatory monitoring periods run of 10 to 30 days. In another embodiment multiple algorithms are run and the output from each includes a confidence value for the diagnosis and a weighting factor. The combination of confidence intervals and weighting factors are used to select the best diagnosis from amongst a set of diagnoses provided by the multiple algorithms. In another embodiment, technician or physician feedback is used to select weighting factors from a limited portion of the data. In another embodiment the weighting factors are specific to a patient.

In a non-limiting example of a patient specific embodiment, a patient may have an atrial conduction disorder that results in an irregular heartbeat but is not classified as atrial fibrillation. An algorithm that uses beat-to-beat irregularity to detect atrial fibrillation may provide false positives based on the irregularity. The technician corrects the false positive result presented by the algorithm and provides the correct diagnosis for this patient's rhythm, and that information is then used by the algorithm to correctly identify future episodes of this particular arrhythmia for this particular patient. The specificity of the algorithm for this patient increases, resulting in more accurate diagnosis, fewer false positives, and lower costs. Additionally, in this case, the system runs multiple algorithms on the patient data stream before presenting any events to the technician. The algorithms include one tuned to detect atrial fibrillation with high sensitivity, one used to detect atrial block conditions, one used to detect atrial fibrillation that results in low HR variability and one that uses atrial fibrillation that results in high HR variability. In one embodiment the results of the multiple algorithm result streams are combined and with accuracy and weighting measures to determine the most likely diagnosis to present to the technician. This reduces the number of false positive events the technician has to deal with and lowers the cost of monitoring the patient.

In another embodiment, the technician runs a Holter scan during a first time period. The detailed technician corrections, interpretations and identification of "normal" and abnormal portions of the ECG signal are then stored and used by the algorithm system to increase specificity for subsequent time periods through the end of the monitoring period. In one embodiment the output diagnoses of the multiple algorithms are weighted based upon the technician input. In another embodiment the multiple diagnoses outputs are combined by use of the weighting and a confidence value calculated for each algorithm.

In another embodiment the weighting is determined by the algorithm sub-system also monitoring the interpretive statements that the technician applies to events generated by the algorithm and uses this information to more accurately provide interpretations or lists of candidate interpretations in subsequent events that it presents to the technician.

In another embodiment the process involves running multiple, different algorithms on a full disclosure data stream or stored full disclosure data and incorporating a voting algorithm to determine which algorithm has the highest specificity, presenting detected events and full disclosure data to a technician, who confirms the algorithms interpretation, incorporating technician feedback into the algorithm to help select the most specific algorithm for a particular patient's morphology and disease state and then continuing to run this personalized algorithm configuration on the patient or the duration of the monitoring period. In another embodiment the full disclosure data is acquired from an ambulatory electrocardiograph.

Another embodiment involves running a specific algorithm on the full disclosure ECG acquired during a first time period, then incorporating the technician's corrections of algorithms classification used in subsequent time periods. Correction includes changing parameters specific to the algorithm. Parameters are selected such that results of the re-configured personalized algorithm displays increased specificity of events presented to the technician during the remainder of the monitoring period.

In another embodiment a library of Electrocardiogram templates is used to create an electrocardiogram that is "clinically equivalent" to the actual patient data. In one embodiment the library is created from a database of electrocardiograms from a broad spectrum of patients. In another embodiment the library is created from prior electrocardiograms taken from the same patient as the actual patient data. In another embodiment the library is further classified into normal and abnormal electrocardiograms based upon the morphology of the peaks in the library and the time of peak widths and peak to peak distances. In another embodiment the classification of the library is used for diagnoses of the actual patient data by matching the actual patient data to the library where matching is done on the basis both of peak morphology and peak to peak timing. In another embodiment the library is used to reduce the data burden on sending ambulatory electrocardiogram data from a remote patient to a care provider. In this embodiment the full disclosure electrocardiogram is acquired from the ambulatory patient, stored locally to the patient and a "clinically equivalent" electrocardiogram is created by matching peak morphology and timing to the library. The clinically equivalent electrocardiogram or the information required to create the same is then sent to the care provider providing a significant reduction in the data sent to the care provider. The data stored local to the patient may be accessed to confirm diagnoses or sent to the care provider at off peak times.

In another embodiment the clinically equivalent electrocardiogram is a visual representation of the electrocardiogram presented at the resolution of the display devices.

MODES FOR CARRYING OUT THE INVENTION

Figure 1:
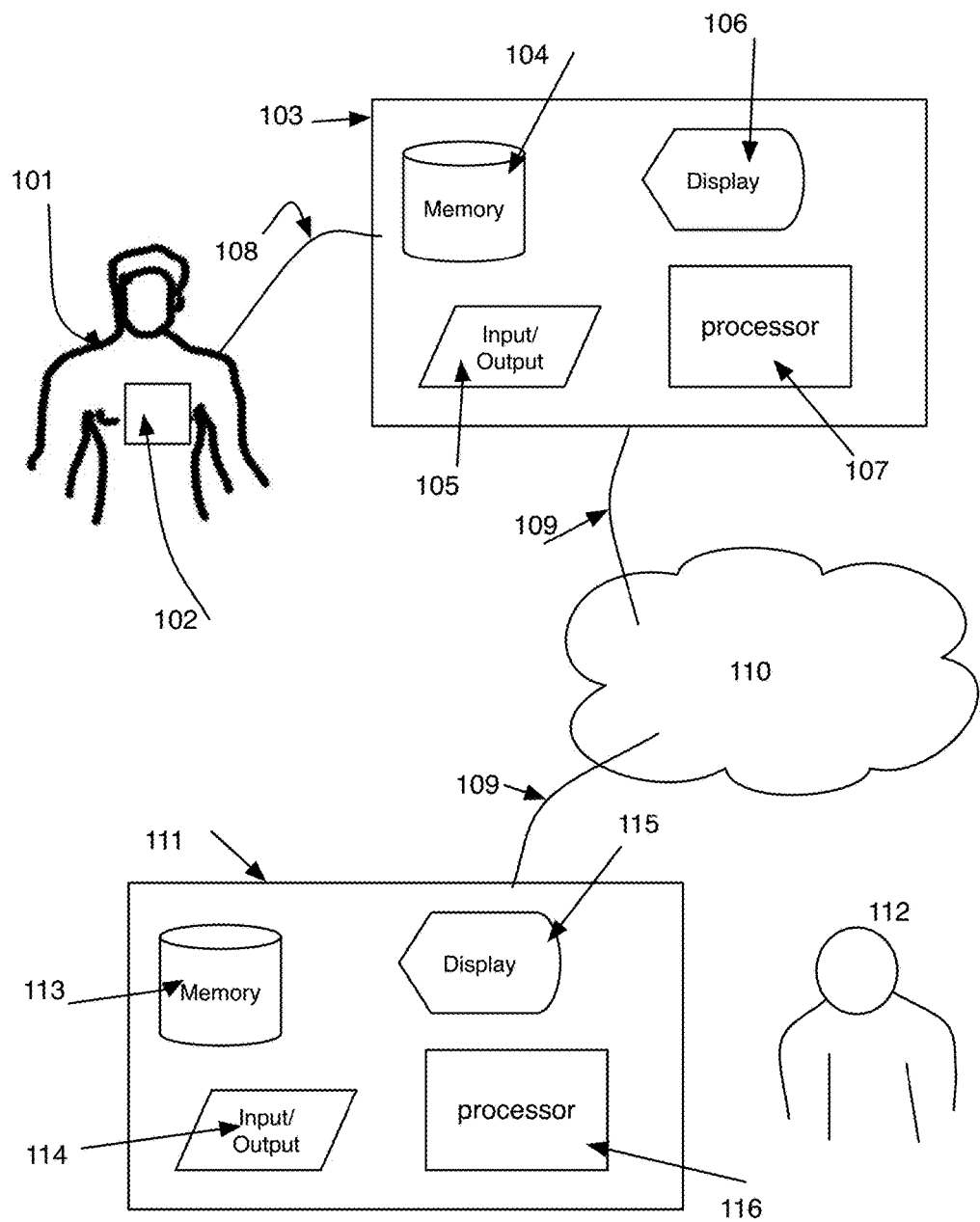
FIG. 1 is a block diagram showing hardware used to practice the invention.

Referring to FIG. 1 systems that may be used to practice the invention are shown. A physiological data acquisition device 102 is attached to a patient 101 and acquires physiological data from the patient. Nonlimiting examples of physiological devices 102 include heart monitors such as would be used to acquire continuous electrocardiogram (ECG) data from a patient such as in a Holter scan as is known in the industry, electroencephalogram (EEG) data, and devices that acquire movement information such as a respiration monitor. The data acquisition device 102 is connected 108 to a computing device 103. The computing device includes input/output (I/O) capabilities 105, memory 104 a display 106 and a processor 107. The connection 108 to the computing device may be by wire or wireless. In the case of wireless, the data acquisition device would therefore logically require transmission capabilities. Data acquired from the patient may be stored locally in memory 104 and may be processed locally by programs running on the processor 107 that are stored in memory 104. The programs may be analysis programs using invented methods, described in detail below that provide diagnoses of the patient's 101 condition. The program parameters may be set using the I/O 105 capabilities and results may be presented locally to patient and/or caregiver via the display 106. In another embodiment the local processor includes only the ability to acquire data from the data acquisition device 102 and to transmit the data to a central processor 111.

The local computing device 103 is connected 109 to a central processing device 111. The connection may be through the Internet, cellular network, local area network or other means known in the art 110.

The central processing device 111 is comprised of a memory 113, input/output 114, a display 115 and a processor 116. A technician or other caregiver 112 operates the central processing device to either provide or confirm diagnoses using methods of the current invention. The technician may also adjust parameters that are used on either the central processing device 111 or the local processing device 103. The technician enters parameters that may be communicated amongst the computing devices through the communication connections already discussed.

Figure 2:
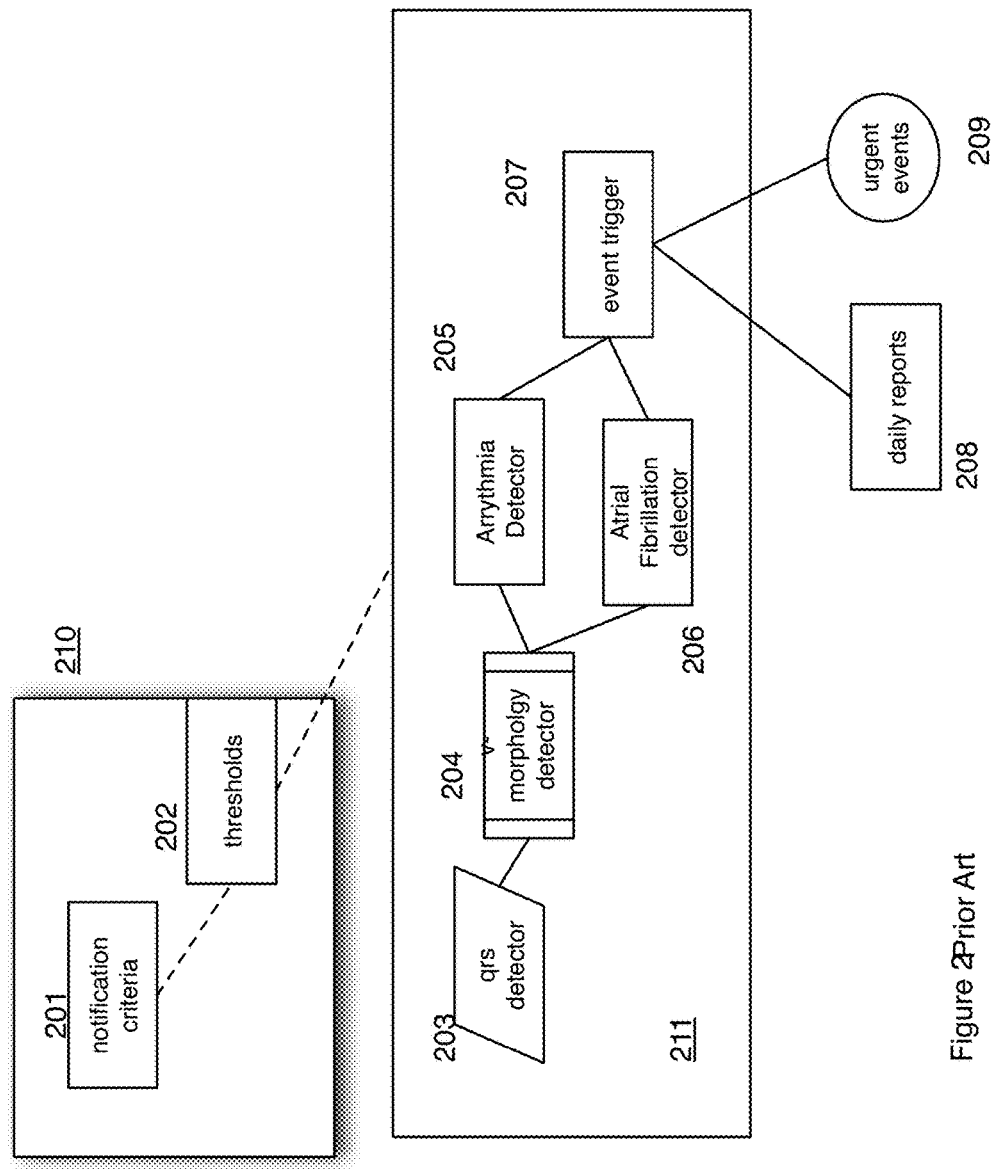
FIG. 2 is a block diagram of a typical prior art analysis algorithm.

Referring now to FIG. 2, a Block diagram of a general medical diagnosis algorithm is shown. Parameters 210 for the algorithm are set. Parameters include notification parameters 201 and calculation parameters 202. The parameters 210 are fed into the algorithm 211. The algorithm is comprised of a detector step 203 that acquires the data from a physiological sensor, a morphology detector 204 that detects characteristic features within the physiological data, diagnostic detectors 205, 206 that detect specific diagnostic features within the characteristic features of the physiological data, an event trigger that accepts diagnostic data from the diagnostic analyses 205, 206 and based upon the parameters 210 either notes in a log 208 or sounds an alarm 209 or both. The morphology detector 204, and the diagnostic detectors 205, 206 also use as input, parameters 202 to guide the automated diagnoses. In one embodiment the output from the diagnostic detectors 205, 206 also include confidence estimates for the diagnoses.

A non-limiting exemplary system that uses the system of FIG. 1 and an algorithm of FIG. 2 is a full disclosure electrocardiogram system. The electrocardiogram data is acquired from the patient and stored in memory of either a local processor or a remote processor or both for subsequent diagnosis. Diagnoses may be completed either locally on a processor located at the patient or remotely after transmitting the physiological data to a central location for analysis. Non-limiting exemplary physiological data includes full disclosure ECG and non-limiting exemplary algorithms include arrhythmia detection algorithms. Non-limiting examples of calculation parameters include thresholds that set upper or lower limits on measured values for heart rate, whether a P wave is detected within the physiological data, values for the integrated area under the P wave within the ECG and signal to noise parameters and the number of consecutive heart beats or time to be included in a diagnosis. The parameters are used collectively by the algorithm to determine whether an atrial fibrillation event has taken place and to calculate a confidence value for that diagnosis. The parameters 210 are specific to the diagnosis algorithm 211. Notification parameters include measured physiological values, which if exceeded, would result in notification of the caregiver of an unusual event. Notification parameters include criteria for immediate notification or logging to a report or both. A non-limiting example of a notification parameter includes limits on heart rate, limits on time variability, and limits on the number of arrhythmia events detected over a given time interval. Should the measured physiological value be above (or below) a first value, the notification parameter directs the system to log an event for a report. Should the notification parameter be above (or below) a second value the notification parameter directs the system to sound an alarm or otherwise indicate an urgent event.

Figure 3:
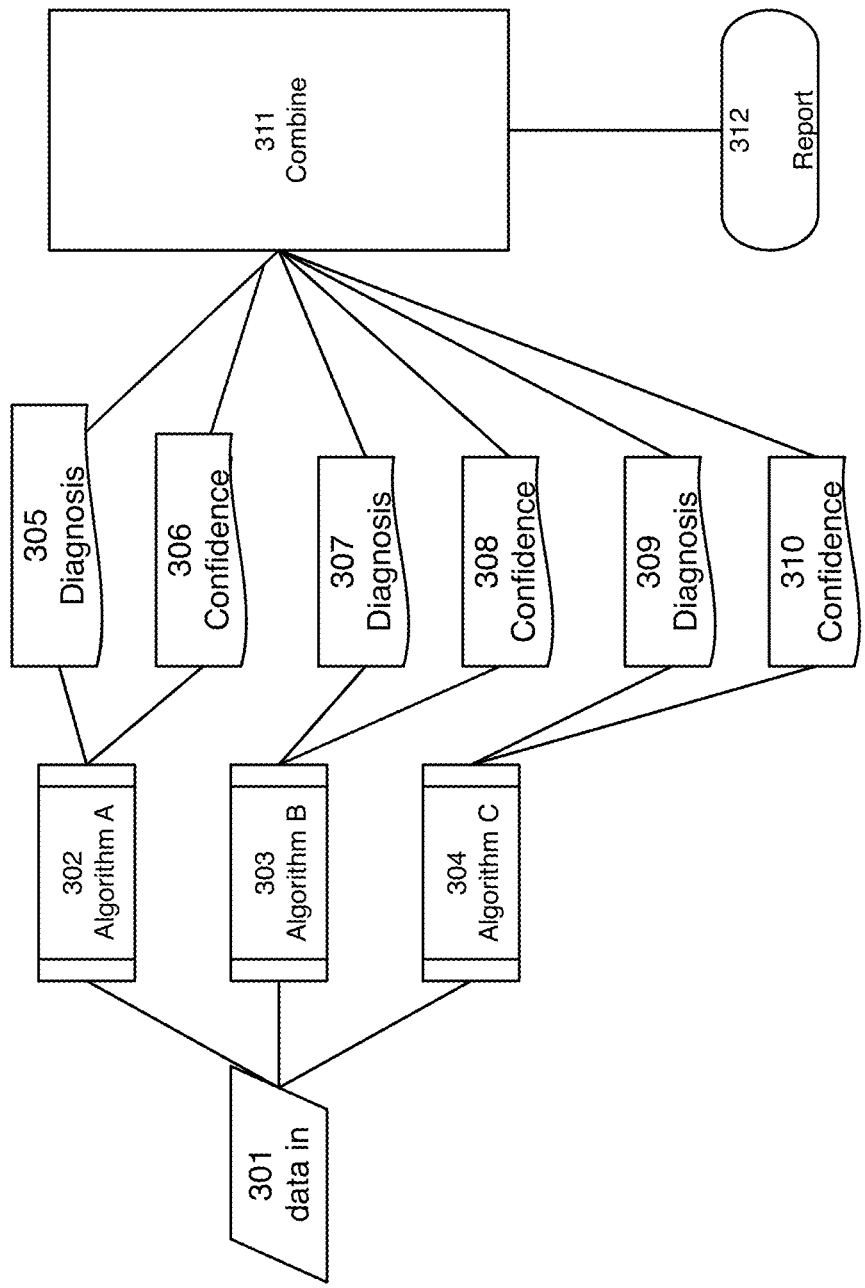
FIG. 3 is a block diagram for a multiple algorithm embodiment.

A first embodiment of simultaneous use of multiple algorithms is shown in FIG. 3. Physiological data is acquired or input 301 and fed to a plurality of algorithms 302, 303, 304. Each algorithm 302, 303, 304 is equivalent to the single algorithm discussed in conjunction with FIG. 2. The algorithms each differ from one another in the method used for estimation of a diagnosis based upon the input physiological data. In one embodiment the multiple algorithms are the same calculation except that the calculation parameters are different for each of the algorithms. In another embodiment the algorithms used different calculation schemes to arrive at diagnoses. Each of the algorithms include an output diagnosis 305, 307, 309 and a confidence estimate 306, 308, 310. The algorithms may be selected based upon their complimentary nature. In one embodiment a first algorithm 302 is selected on the basis of providing high sensitivity but low selectivity to detecting a physiological anomaly but is prone to give erroneous false positive results on input data with low signal to noise. A second algorithm 303 is selected with complimentary performance of low sensitivity but high selectivity and performs with fewer false positive reports of the same physiological anomaly with low signal to noise data. With high signal to noise data the confidence estimate of the first algorithm 302 is higher and the confidence estimate of the second algorithm 303 may be relatively lower. The reverse would be true in the case of low signal to noise data. A third algorithm 304 may be selected with performance relative to signal to noise that is intermediate to that known of the other two algorithms 302, 303. The output of all the algorithms is combined 311 to produce a single diagnosis report 312. In one embodiment the combination is a weighted average of the diagnoses 305, 307, 309 from each of the algorithms. In another embodiment the weighting factors are the confidence estimates 306, 308, 310 from each of the algorithms. In another embodiment the weights are pre-selected factors selected by running the algorithms on physiological databases with confirmed diagnoses.

A non-limiting exemplary application of the multiple algorithm approach is in the interpretation of ECG Holter data. In this example two AF detector algorithms work in parallel and generating AF onset/offset signals. One of the AF detector algorithms is more accurate when HR variability is relatively low, and another one is producing better results when HR variability is high. Both AF detector algorithms "know" their range of HR variability and they are outputting a corresponding confidence measure (weight) along with their decision. The results are combined as a single weighted outputs from both AF detector algorithms and calculates a final result. For an ECG rhythm with a high HR variability, the first algorithm is more accurate and it will have a higher weight with its decision. But when HR variability is low, the second algorithm will have higher weight in final result. Therefore, final output will be weighted more heavily from the "right" algorithm.

Figure 4:
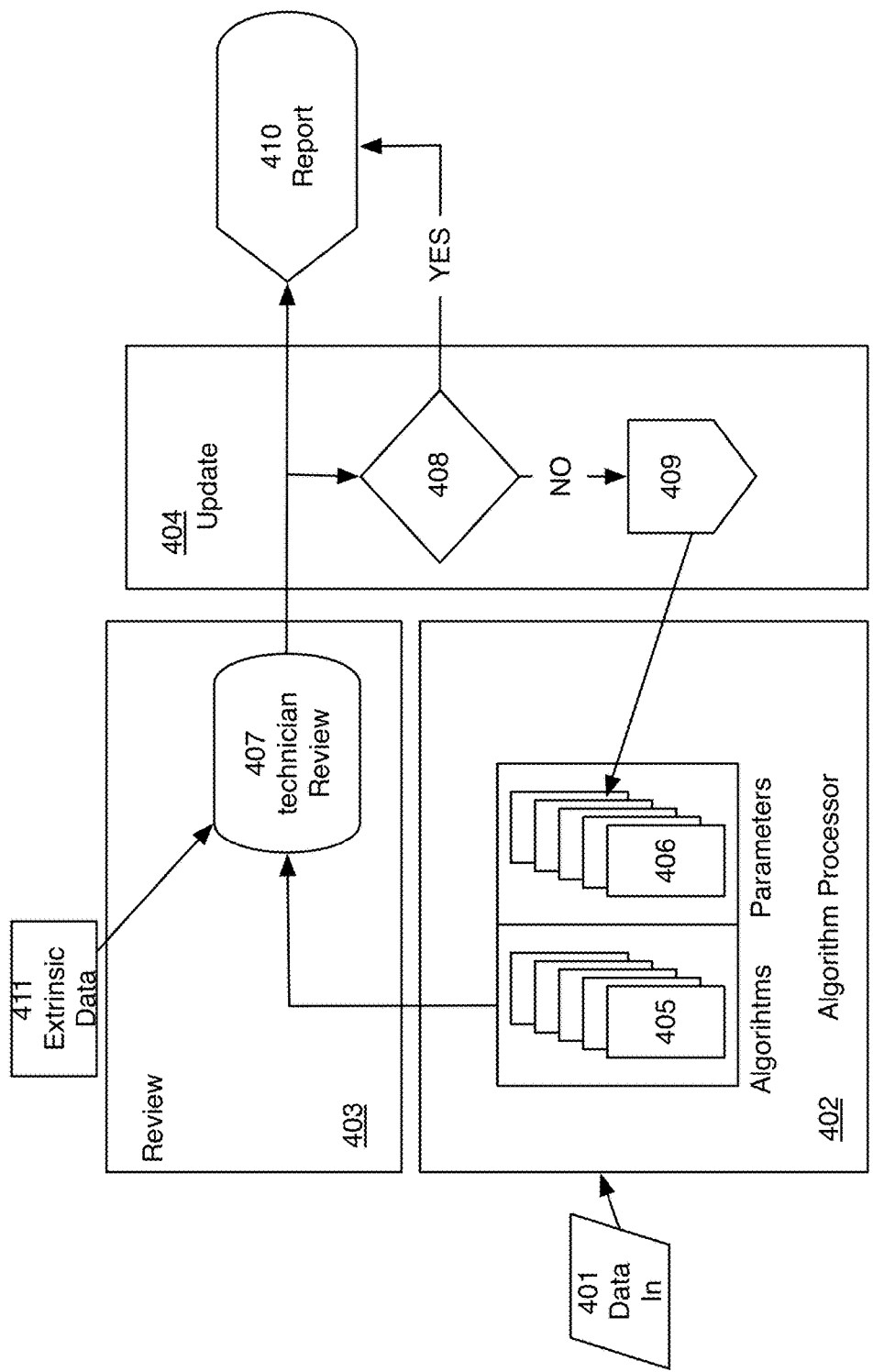
FIG. 4 is a block diagram for an adaptive multiple algorithm processing embodiment.

A second multiple algorithm approach is shown in FIG. 4. Physiological data 401 is input into a multiple algorithm processor 402. Output from the processor is passed to a technician review process 403. The results of the review are passed to an update process 404 and also to a reporting process 410. The algorithm processor 402 is comprised of a plurality of algorithms 405. Each algorithm has an associated set of calculation parameters 406. Calculation parameters are as defined and discussed earlier in conjunction with FIG. 2. Output from the multiple algorithms is passed to the review process 403. Output may include multiple diagnoses, one from each algorithm or may include a single combined output as discussed earlier in conjunction with FIG. 3. The technician reviews the diagnostic output 407. Review may include incorporation of extrinsic data 411. Extrinsic data may include information of which the technician is aware that cannot otherwise be incorporated into an automated algorithm. In one embodiment extrinsic data is patient specific information that is known to affect the diagnosis. Nonlimiting examples of extrinsic data include: recent medication of the patient, movement of the patient, physical position of the patient, such as standing, sitting or lying down, unusual health traits of the patient, such as a patient known to have unusually strong cardiovascular fitness, or, unusually weak cardiovascular fitness, and whether the patient is fit with a pacemaker. The technician review passes to an update process 404 where a decision 408 is made as to the accuracy of the diagnosis. If the diagnosis is determined to be accurate (the "YES" branch) the results are reported 410 and the algorithms parameter sets are left unchanged. If the diagnosis is determined by technician review to be inaccurate the parameters for those algorithms that are known to be inaccurate are adjusted 409 and the calculation parameters 406 are updated. In one embodiment the calculation parameters are updated generally for all future calculations. In another embodiment the calculation parameters are thereby specific to a particular data set. In another embodiment the calculation parameters are thereby specific to a patient.

Figure 5:
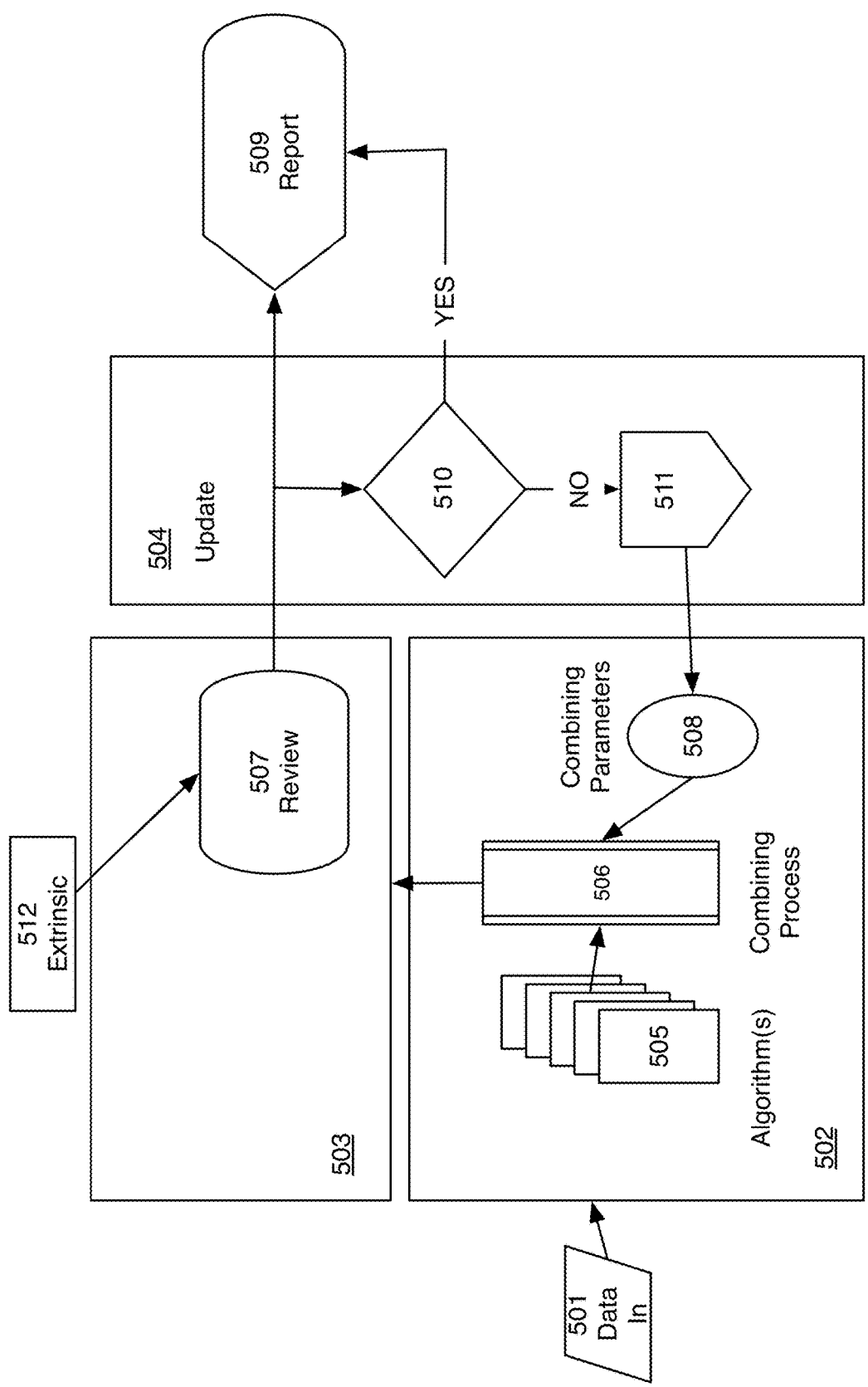
FIG. 5 is a block diagram for a second adaptive multiple algorithm embodiment.

In another embodiment shown in FIG. 5 a multi-algorithm adaptive approach is shown. Physiological input data 501 transferred into a multiple algorithm processor 502. Output from the processor is fed to a review process 503. In one embodiment, the review process uses extrinsic data 512. Extrinsic data is as already discussed in conjunction with FIG. 4. The technician review results are passed to an update process 504 and results are reported to a caregiver 509. In the preferred embodiment, the algorithm processor 502 is comprised of a plurality of algorithms 505. In another embodiment, the algorithm processor 502 is comprised of a single algorithm. Each algorithm includes calculation parameters (not shown) as already discussed. The processor 502 further includes a combining process 506. The combining process 506 combines the results of the multiple algorithms 505 to produce a single diagnosis based upon the physiological data 501. The combining process is governed by combining parameters 508. In one embodiment the combining process is a weighted average of the results from the multiple algorithms 505. In another embodiment the combining process combines the results of the multiple algorithms weighting each by a pre-selected weighting parameter. In another embodiment the results of the multiple algorithms are combined through a weighted average where the weighting is both a confidence estimate from the algorithm as well as a pre-selected weighting. The output from the diagnosis is reviewed 507 by a technician. In one embodiment extrinsic data 512 is used by the technician. Extrinsic data may include patient health information pertinent to the diagnosis that cannot be included in the algorithms 505. Nonlimiting examples of extrinsic data include: recent medication of the patient, movement of the patient, physical position of the patient, such as standing, sitting or lying down, unusual health traits of the patient, such as a patient known to have unusually strong cardiovascular fitness, or, unusually weak cardiovascular fitness, and whether the patient is fit with a pacemaker. The technician review passes to an update module 504. The update module includes a decision 510 to change the parameters of the algorithm processor 502 or leave them the same. If the technician review indicates the diagnosis is accurate, the decision then would be to leave the algorithm as is and report the results 509 (the "YES" branch). If the diagnosis is found to be wrong the parameters 508 of the combining process 506 are updated 511 and sent to the multiple algorithm processor 502 (the "NO" branch of 510). In one embodiment the combining parameters 508 are weighting parameters to be used in combining the output of the multiple algorithms. In another embodiment the combining parameters are weighting factors derived by optimization of the weighting from prior processing of a physiological database with known diagnosis results. In one embodiment the weighting parameters are updated generally for all future calculations. In another embodiment the weighting parameters are thereby specific to a particular data set. In another embodiment the weighting parameters are updated based upon extrinsic information 512 that is specific to a patient and the weighting parameters are thereby specific to a patient.

In a non-limiting example of the adaptive embodiment of FIG. 5, electrocardiogram data such as Holter scan data is analyzed using multiple algorithms. Some of the multiple algorithms demonstrate good sensitivity and +P for some patients while they could be consistently wrong for some other patients. In this case the technician review input to the update would be to increase weighting factor for "right" algorithms while other algorithms would receive a penalty in weighting factor every time they produce a wrong output. The multiple algorithm approach would thereby adapt over time to provide more accurate diagnosis. In one embodiment, the adaptation scheme for the weighting factor could be an exponential moving average of binary inputs of (0,1) where "1" corresponds to a correct output of the algorithm and the "0" corresponds to an incorrect algorithm diagnosis.

Figure 6:
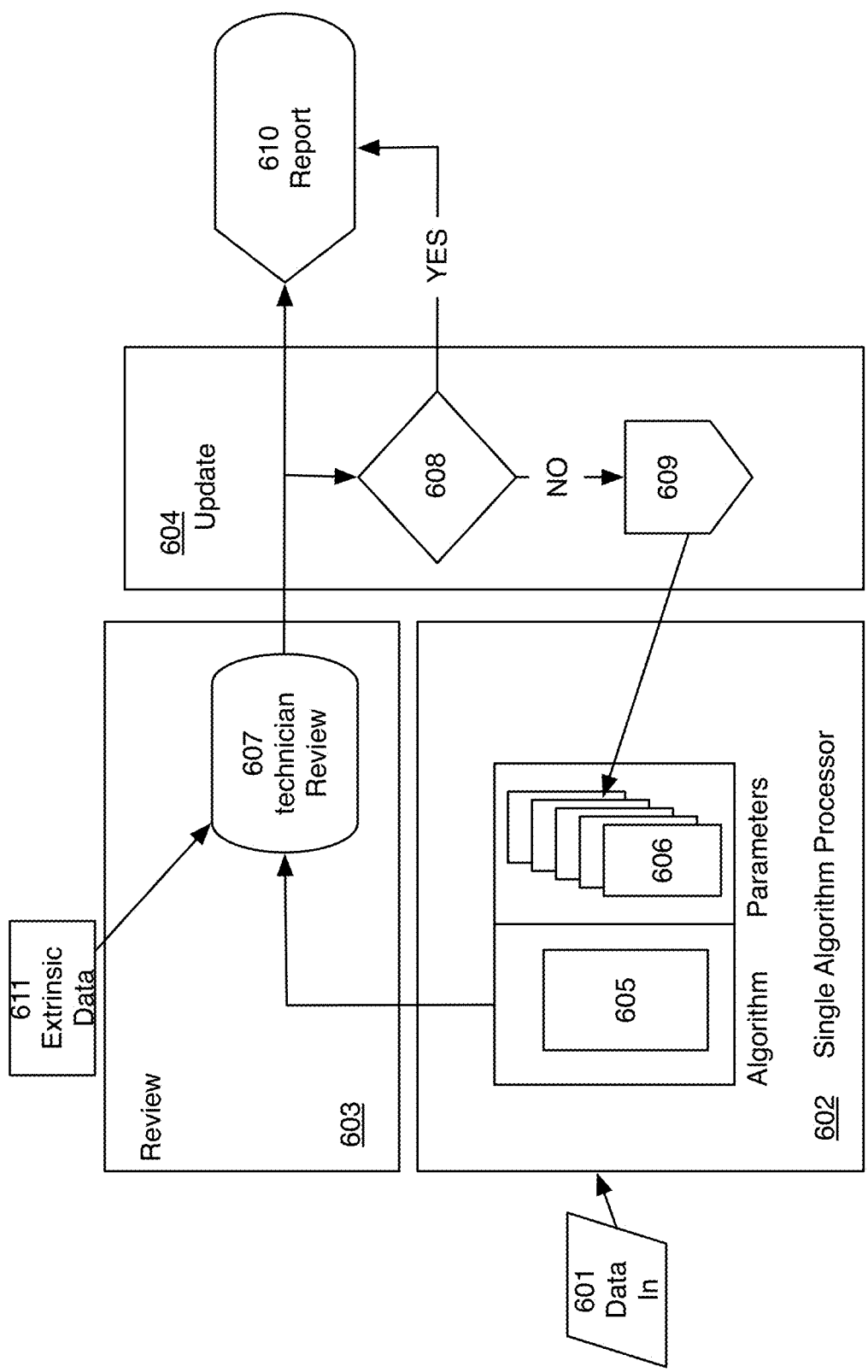
FIG. 6 is a block diagram for a third adaptive multiple algorithm embodiment.

Another embodiment shown in FIG. 6 includes a single algorithm with a plurality of input parameters. The parameters are known to affect the diagnosis output of the algorithm. Physiological data 601 is input into the algorithm processor 602. Multiple parameters 602 control the algorithm.

Output from the processor is passed to a technician review process 603. The results of the review are passed to an update process 604 and also to a reporting process 610. The algorithm processor 402 is comprised of a single algorithm 605. The algorithm has an associated set of calculation parameters 606. Calculation parameters are as defined and discussed earlier in conjunction with FIG. 2. Output from the algorithm is passed to the review process 603. Output may include multiple diagnoses, one from each parameter set or may include a single combined output as discussed earlier in conjunction with FIG. 3. The technician reviews the diagnostic output 607. Review may include incorporation of extrinsic data 611. Extrinsic data may include information of which the technician is aware that cannot otherwise be incorporated into an automated algorithm. In one embodiment extrinsic data is patient specific information that is known to affect the diagnosis. The technician review passes to an update process 604 where a decision 608 is made as to the accuracy of the diagnosis. If the diagnosis is determined to be accurate (the "YES" branch) the results are reported 610 and the algorithm parameter set is left unchanged. If the diagnosis is determined by technician review to be inaccurate the parameters are adjusted 609 and the calculation parameters 606 are updated. In one embodiment the calculation parameters are updated generally for all future calculations. In another embodiment the calculation parameters are thereby specific to a particular data set. In another embodiment the calculation parameters are thereby specific to a patient.

In summary of the embodiments of FIGS. 4, 5, and 6, FIG. 4 is an adaptive process where multiple algorithms are run and combined to provide a diagnosis results. The adaptive nature of the embodiment shown and discussed in FIG. 4 is that calculation parameters specific to each algorithm are updated based upon technician review. The adaptive nature of FIG. 5 is that the combining parameters are updated based upon technician review. The combining parameters dictate how the results of the multiple algorithms will be combined but do not affect how the individual algorithms process the physiological data to reach a diagnosis. FIG. 6 shows an analysis system that includes a single algorithm that uses plurality of controlling parameters. The controlling parameters are adjusted based upon technician review or analysis of a database of known results. In another adaptive embodiment both the calculating parameters as discussed in FIG. 4 and the combing parameters as discussed in FIG. 5 are updated. It should be understood and is implied throughout this document that multiple embodiments can be combined.

In another embodiment applicable to all of the methods of FIGS. 4-6, a first set of data is acquired on day 1 of a multiple day test. A technician reviews 407, 507, 607 the day one results, flags abnormalities and confirms a diagnosis. The review then results in an update 404, 504, 604 of the algorithm parameters, weighting factors and combining factors for the algorithms. The updated factors being used on days 2 through the end of the test.

Referring now to FIGS. 7-12 embodiments that include creations, transmission and interpretation of "clinically equivalent" electrocardiograms from actual full disclosure electrocardiogram are shown. A clinically equivalent electrocardiogram is one that would result in the same diagnosis as the original electrocardiogram data. The diagnostically equivalent electrocardiogram data is created in a way as to make a more compact data set or a data set that is more readily interpreted. It is more than data compression techniques that are known in the art.

Figure 7:
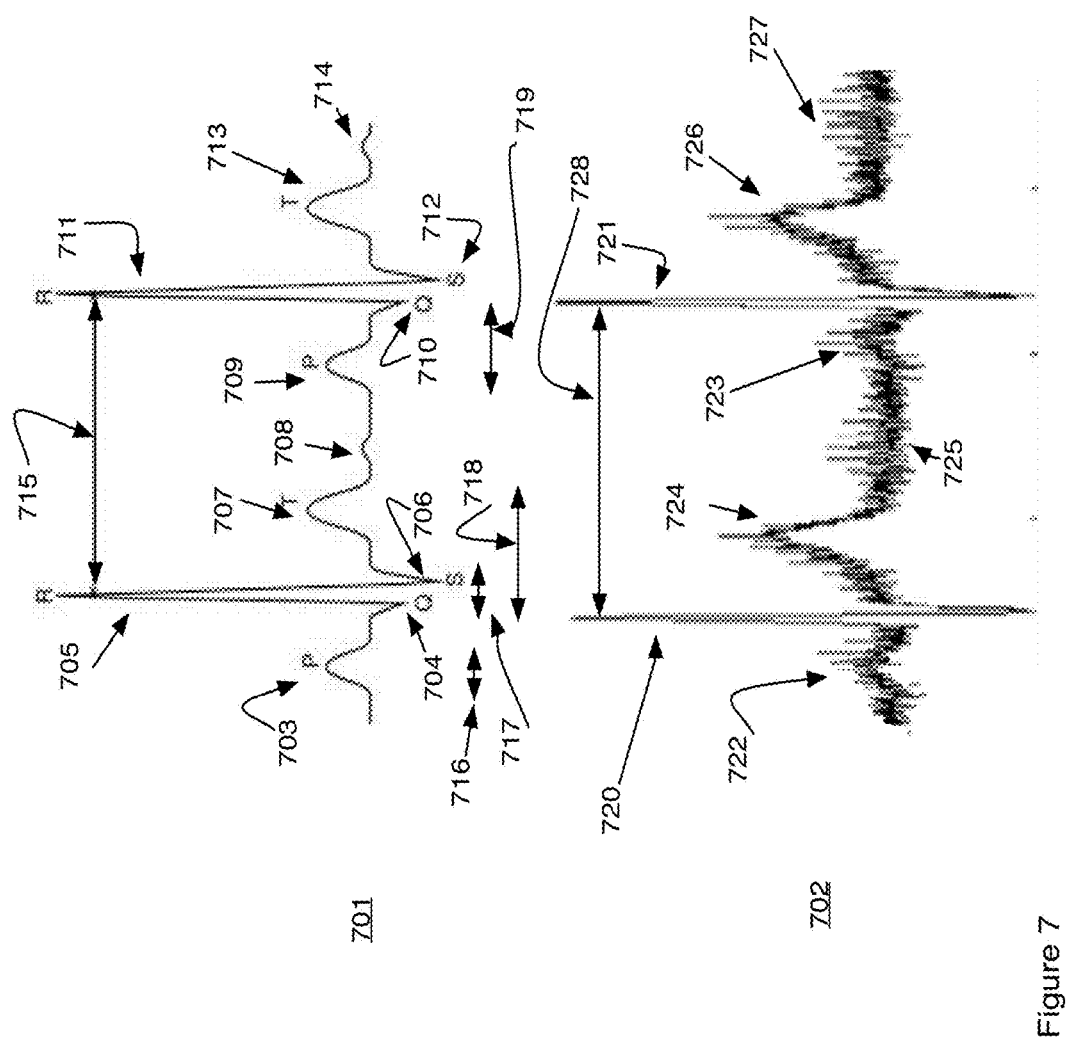
FIG. 7 is a diagram showing both actual electrocardiogram data and a clinically equivalent version of the data.

FIG. 7 shows a diagnostically equivalent electrocardiogram 701 that was created from the original electrocardiogram 702. The electrocardiogram is one that might be considered a normal, healthy electrocardiogram. The components of the electrocardiogram include the P 703, Q 703, R 705, S 706, T 707, and, U 708 peaks or waves of a single heart beat cycle repeated at an interval 715 or the distance between the R peaks of the two consecutive beats shown. Diagnoses of the health of an individual showing such an electrocardiogram is made on the basis of the existence of each of the peaks 703-714, the shapes of the peaks 703-714 and time intervals that describe the peak widths and distance between peaks. Shape of the peaks includes the peak height, the symmetry and the peak width. Non-limiting example time intervals include the distance between consecutive R peaks 715 that is also commonly used for the heart rate, the width of the P peak 716, the width of the Q, R, S complex 717, the time 718 from the start of the Q to the end of the T peaks, and, the time 719 from the start of the P to the Q peak. The diagnostically equivalent electrocardiogram 701 includes the same features scaled to the time intervals and with peak intensities and shapes that would be interpreted the same as the data in the actual electrocardiogram 702. In the example shown the P wave corresponds to the P-wave 703 the T wave 724 corresponds to the T-wave 707. The U wave 708 corresponds to the U wave 725 and the QRS waves 704, 705, 706 correspond to the same in the QRS complex 720 of the actual data. The timing of the peaks in the diagnostically equivalent ECG 701 is the same as the timing in the raw data ECG 702. Only one time interval 728, the R to R time is labeled in the original raw data ECG 702 but it should be understood that all the time intervals 715-719 in the diagnostically equivalent ECG 701 are chosen such that the diagnosis from the original ECG 702 would be the same whether viewing the diagnostically equivalent ECG 701 or viewing the originally acquired ECG 702. In one embodiment the series of peaks 703-708 in one entire beat of the diagnostically equivalent ECG 701 are selected from a library of ECG beat patterns. In another embodiment the individual peaks 703-708 in the diagnostically equivalent ECG are selected from a library of peaks. In one embodiment the libraries (either of entire single beats or of individual peaks) are constructed from observing the ECG's of a plurality of patients, doing curve fitting to create the diagnostically equivalent ECG library and storing the library for comparison with ECG's acquired later. In another embodiment the libraries (either of entire single beats or of individual peaks) are constructed from observing the ECG's of a single patient at different times and in different health conditions. These are then analyzed, curve fit and stored for comparison with an ECG acquired later from the same patient.

Figure 8:
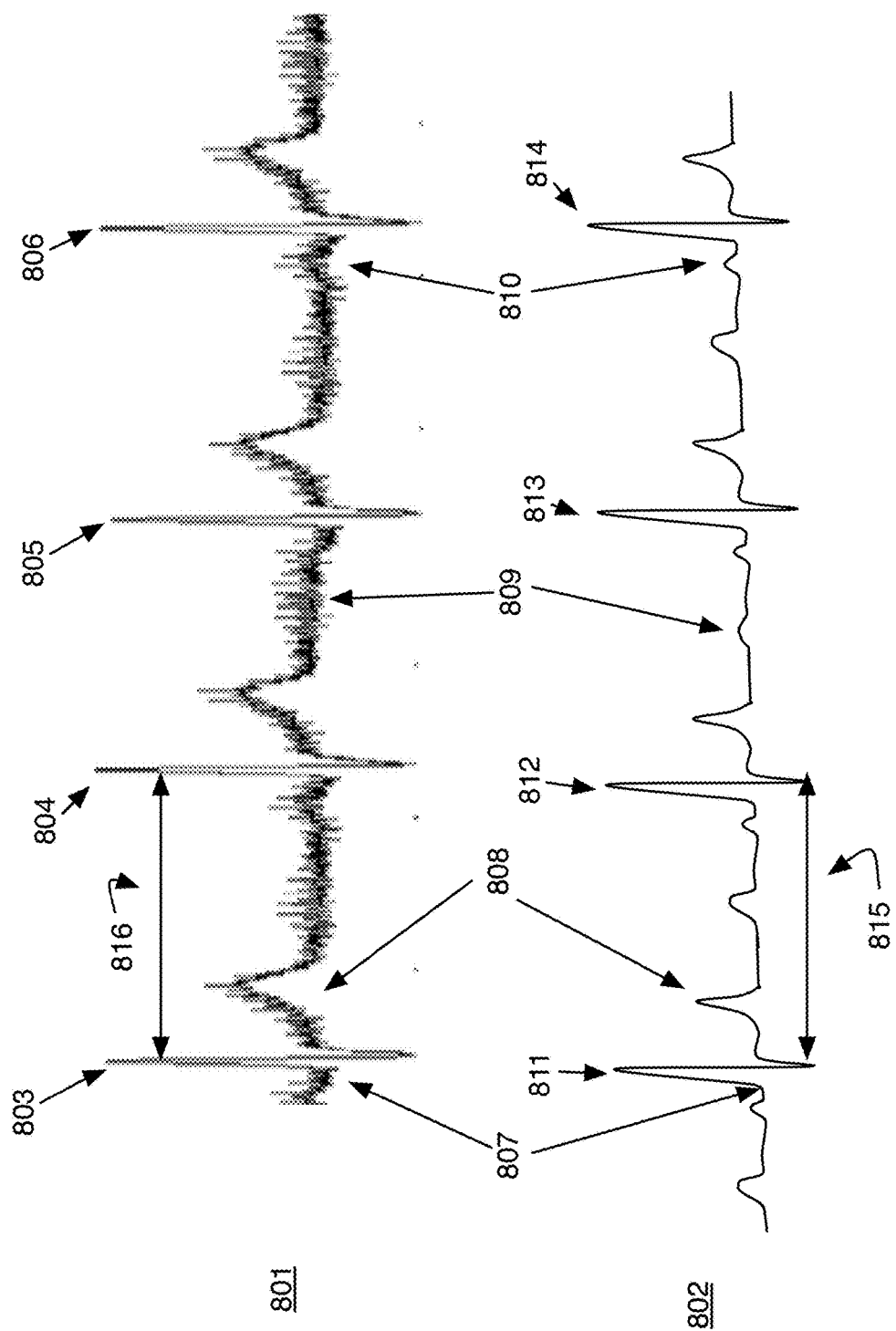
FIG. 8 is a diagram showing actual and clinically equivalent data and the points of correspondence between the two.

FIG. 8 provides further insight into creating a diagnostically equivalent ECG 802 from an ECG 801. The source ECG includes a series of four beats, with the R-peak of each labeled as 803, 804, 805 and 806. The diagnostically equivalent ECG 802 includes the same number, four, beats with the corresponding R-peaks labeled 811, 812, 813 and 814 respectively. The diagnostically equivalent ECG 802 includes the same features and timing as the original data 801. In one embodiment the diagnostically equivalent ECG is created from a library of peak images each selected by matching the morphology of the peak in the library with that seen in the original data 801. In another embodiment the diagnostically equivalent ECG 802 is created from a library of ECG images where the ECG image selected from the library is the one that most closely matches the original data 801 in terms of the same set of peaks in the same relative intensity and each of the peaks having the same morphology and the timing between peaks most nearly matches that of the original data. In one embodiment the diagnostically equivalent ECG is selected from a library of ECG's where the library ECG is selected as the nearest match to the original data 801 in terms of relative intensity of the and peak morphology for each of the individual beat patterns and the timing between peaks in diagnostically equivalent ECG 802 is selected to match that of the original data 801 by scaling of the time axis (horizontal axis) of the ECG's selected from the library of ECG's. In the example shown the R-peaks 811, 812, 813, 814 in the diagnostically equivalent ECG 802 are selected from the library of ECG images such that their morphology each match the morphology of consecutive R-peaks 803, 804, 805, 806 respectively in the original data 801. The spacing 815 between the R-peaks in the diagnostically equivalent ECG 802 is scaled to match that of the spacing 816 in the original data 801. The spacing between each of the R-peaks 811-814 is scaled in the same fashion to the corresponding distance between r-peaks 803-806 in the original data 801. Only the first spacing is labeled in the FIG. 8. Similarly other peaks in the diagnostically equivalent ECG 802 are selected from a library of peaks by matching morphology, relative intensity and scaling for timing. As examples the Q-Peak 807 in the original data is seen to be barely visible if at all and this is also seen in the corresponding spot in the diagnostically equivalent ECG 802. The same is true of the labeled t-peaks 808 and u-peaks 809 and p-peaks 810. Again in one embodiment each of the peaks is selected individually from a library of peaks by matching peak morphology and their locations along the time (horizontal) axis is matched to the location in the original data ECG 801. In another embodiment the peaks in the diagnostically equivalent ECG are selected from a library of ECG complete beat patterns that includes peaks P, Q, R, S, T and U and whose morphology and relative intensity most nearly matches that in each of the individual beats seen in the original data and the selected complete beat patterns are then scaled along the horizontal axis to match that seen in the original ECG data 801.

Figure 9:
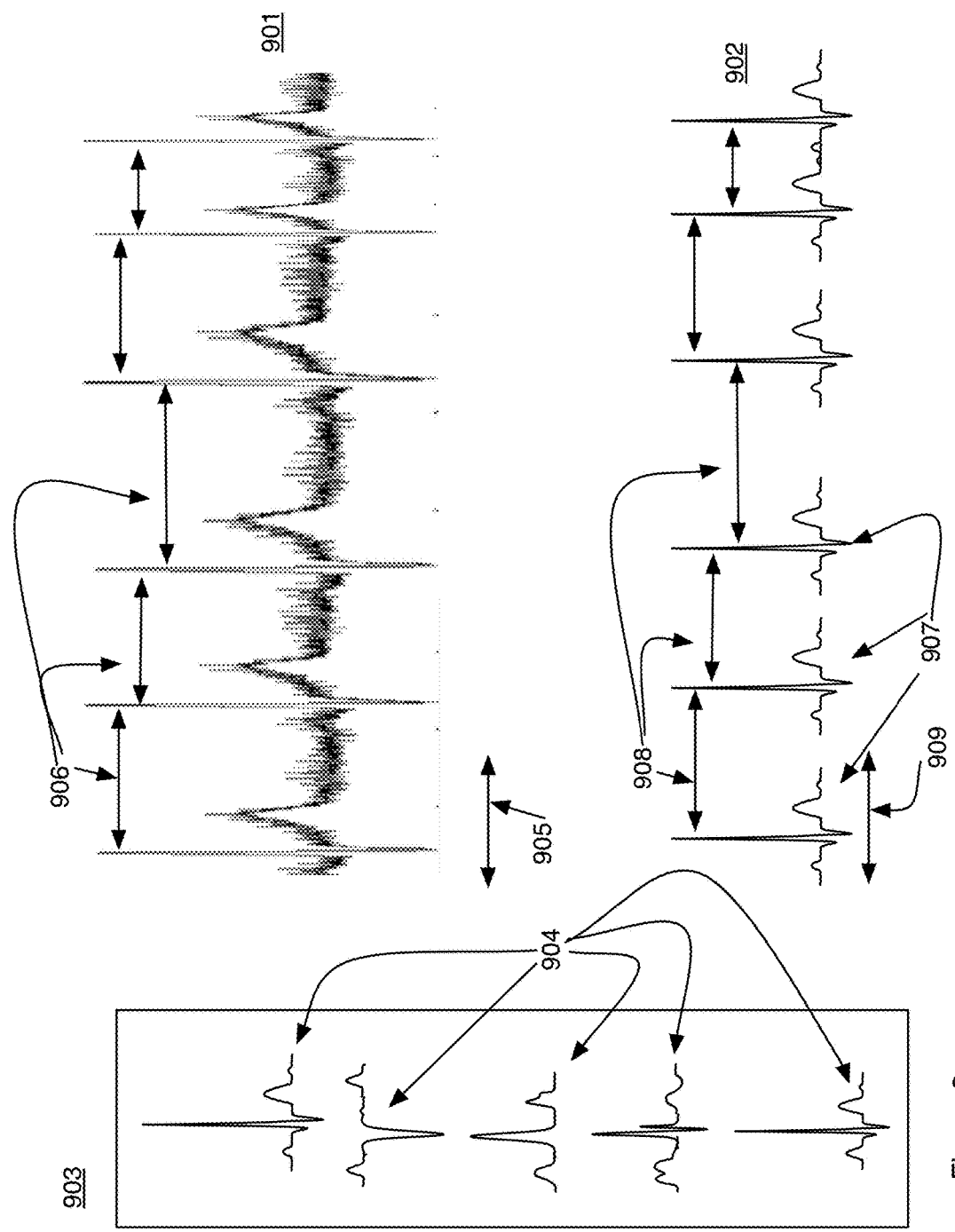
FIG. 9 is a diagram showing actual electrocardiogram data and clinically equivalent data constructed from a first embodiment of a library of electrocardiogram templates.

Referring now to FIG. 9, an embodiment where the peak library is comprised of images of complete beat patterns is shown. The original ECG data 901 is comprised of a series of peaks (P, Q, R, S, T, U not labeled) where individual R peaks are separated by a time 906. The separation 906 is defined conventionally as the beat interval and the number of intervals 906 per minute is the heart rate. The distance between peaks 906, 905 can be used to scale the distance between peaks 908, 909 in the diagnostically equivalent ECG 902. The individual beat patterns 907 in the diagnostically equivalent ECG are selected to match the morphology of the peaks in each of the individual beats 905 of the original ECG data 901. The library of ECG beat patterns 903 is comprised of a plurality of individual beat patterns 904. The selected beat patterns are then scaled along the horizontal axis 905 such that the distance between consecutive R peaks in the scaled diagnostically equivalent ECG 902 matches the corresponding distances 906 in the original ECG data 901. In one embodiment the library is constructed from observed ECG on a plurality of patients who displayed the indicated ECG and whose corresponding heart status was confirmed by a clinician. There is a lookup table of diagnoses for each of the plurality of beat patterns 904 in the library 903. In some cases the beat patterns correspond to normal beat patterns observed over a plurality of patients. In other case the beat patterns are linked to a particular heart event such as arrythmias, sinus bradycardia, sinus tachycardia and others as are known in the art. A match of the ECG data 901 to ECG patterns from the library 903 can then be used through the lookup table to diagnose the status of the patient via their ECG data 901. The library of raw ECG data is further used to confirm that the diagnostically equivalent ECG 902 is in fact diagnostically equivalent in that the raw data ECG 901 and the constructed image 902 would result in the same diagnosis made by a clinician be that a doctor or ECG technician.

Figure 10:
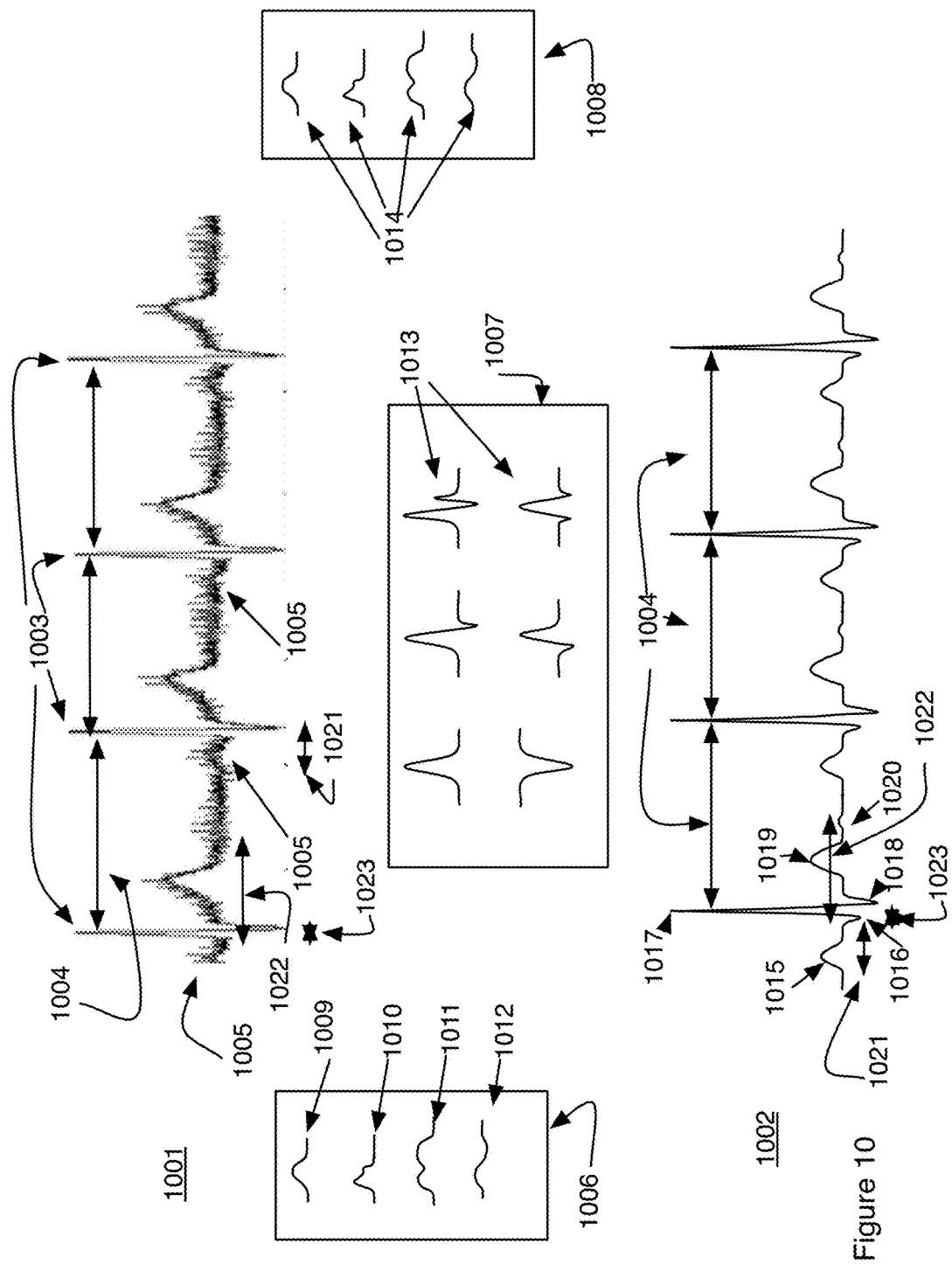
FIG. 10 is a diagram showing actual electrocardiogram data and clinically equivalent data constructed from a second embodiment of a library of electrocardiogram templates.

In another embodiment shown in FIG. 10, the library is comprised not of beat patterns as in FIG. 9 but rather in individual peaks that would be observed in an ECG. In this embodiment a diagnostically equivalent ECG 1002 is created from clinical ECG data 1001 by matching the morphology of each of the peaks in the ECG data 901 with peaks having the same morphology that are in libraries 1006, 1007, 1008 of peaks. As a non-limiting example the first peak 1005 (shown only partially in the first beat) is identified as a P-peak and a library of P-peaks 1006 is searched to most closely match the morphology of the observed P-peak. The best match is determined by a least square fit of each of the peaks in the library to the peak data 1005 in the observed ECG data 1001. In the example shown the best match for the P-peak is selected from a library of P-peaks 1006. The best match visually from the peaks (1009-1012) is the first peak 1009 in the library. This peak is then selected for the diagnostically equivalent ECG 1002 and is shown as peak 1015. Similarly, the other peaks in the original ECG data 1001 are matched for their morphology with peaks in a library. For example, the R peaks 1003 are compared to a library 1007 of R-peaks. The library comprising a plurality 1013 of R-peaks and the best match is then used in the diagnostically equivalent ECG 1002. In one embodiment the libraries 1006-1008 are created from curve fitting to ECG's observed from a plurality of patients whose ECG have been analyzed by a clinician and the patient health status has been diagnosed and confirmed. In another embodiment the libraries 1006-1008 are created from curve fitting of peaks observed in an ECG from the same patient whose ECG data 1001 is being analyzed. The library created from ECG's observed at a time different than the time at which the ECG data 1001 is acquired. In one embodiment the library from the same patient is comprised of peaks where the condition of the patient at the time the peaks were observed was confirmed by a clinician. In this manner a health episode particular to the patient can be flagged by watching for a repetition of the same ECG. In another embodiment the "normal" ECG can be determined for the particular patient that may be different from a normal ECG for a plurality of other patients. The normal ECG peculiar to the particular patient can then be matched in subsequent ECG and avoid false positive alarms that would occur if comparing the patient's ECG to a library of ECG's from other patients.

In one embodiment the timing of the ECG in the Diagnostically equivalent ECG 1002 can be scaled to match the timing observed in the ECG data 1001 by measuring particular timing intervals in the ECG data and scaling the diagnostically equivalent ECG 1002 to match these intervals. Nonlimiting examples of such characteristic time intervals include the time 1004 between consecutive R-peaks, the width 1023 of the QRS complex, the time 1021 from the start of the P-peak to the start of the Q-peak, and the time 1022 from the start of the Q-peak to the end of the T-peak and the width (not labeled) of each of the peaks (P, Q, R, S, T and U) observed in the ECG. In one embodiment the location and width of each peak in the diagnostically equivalent ECG 1002 are scaled to match the corresponding width and timing location of each of the peaks observed in the observed ECG data 1001. The diagnostically equivalent ECG 1002 is shown in the example as including the same number of peaks as that observed in the ECG data 1001. In one embodiment the diagnostically equivalent ECG is a composite of the observed data and a smaller number of peaks than in the raw data ECG 1001 are presented in the diagnostically equivalent ECG. That is if the series of beats in the observed data 1001 result in a series of beats in the diagnostically equivalent ECG that are all identical much as is shown in the Figure. The diagnostically equivalent ECG may be further condensed to show only those exemplary peaks that are different from one another.

Figure 11:
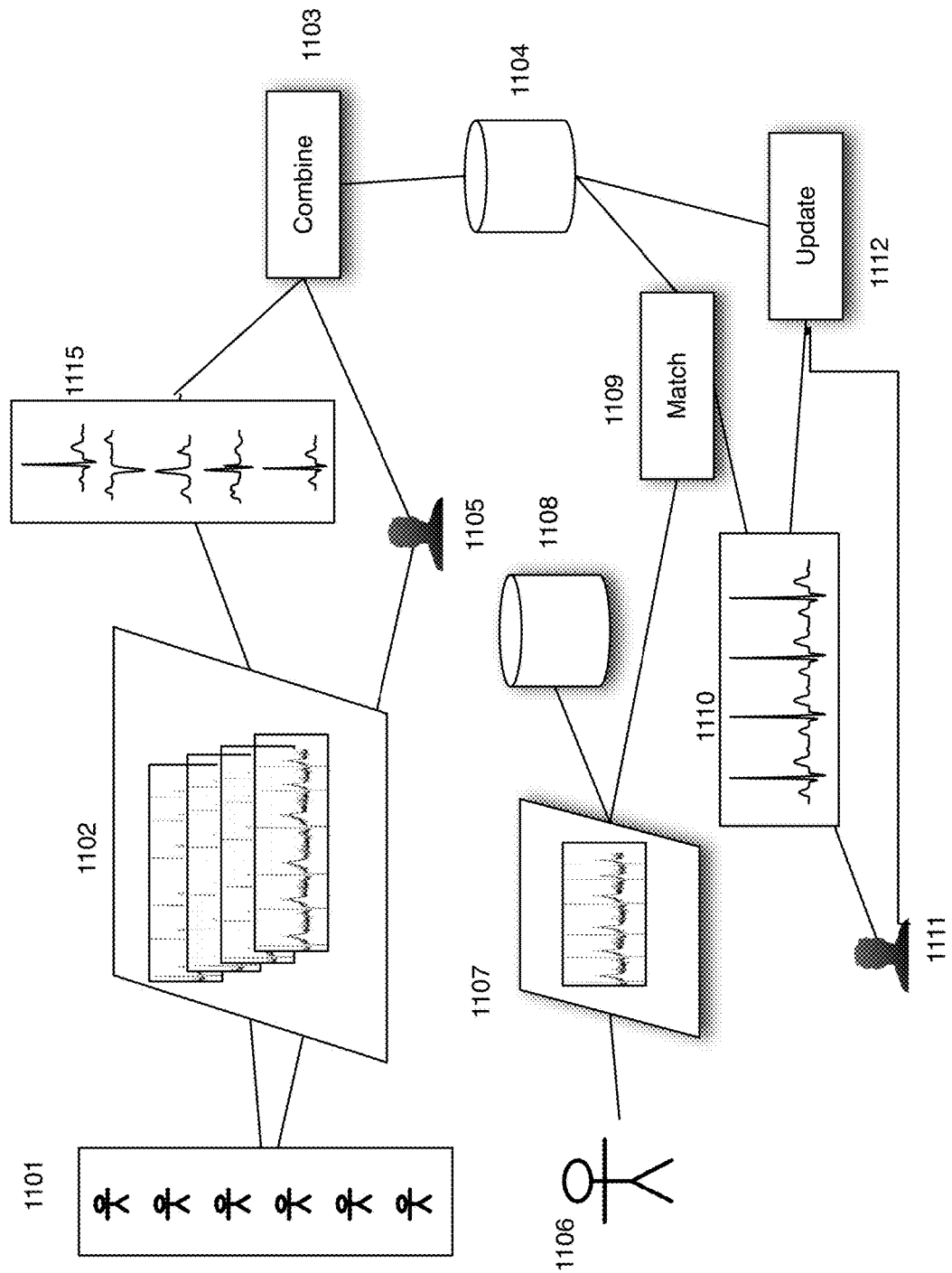
FIG. 11 is a flow chart showing construction of a clinically equivalent electrocardiogram from actual data where the template library is created from a broad spectrum of patient's electrocardiograms.

A flow chart of an exemplary use of the methods is shown in FIG. 11. Electrocardiograms 1102 are obtained from a plurality of patients 1101 are recorded and then filtered and in some embodiments curve fit for smoothing to provide a plurality of example ECG beats 1115. A clinician analyzes 1105 the plurality of ECG's either as the raw data ECG's 1102 or as the smoothed and curve fit ECG's 1115 providing a diagnoses of the patient's conditions and flagging ECG's that represent abnormal health events. The diagnoses may include observation of the patients 1101 at the same time as acquiring the ECG's 1102. The diagnoses and the ECG images 1115 are combined 1103 and stored 1104 in a database. Combination and storage may include a tabular format wherein particular ECG images are associated with particular health diagnoses such that at a later time if a particular diagnostically equivalent ECG is created from patient ECG data and the diagnostically equivalent ECG is a selection from a particular ECG in the stored library 1104, the diagnoses associated with the diagnostically equivalent ECG is provided as a diagnoses for the health condition of the patient whose patient ECG data resulted in the diagnostically equivalent ECG. The combination process 1103 further includes a comparison by a technician of the diagnoses table with his interpretation of the raw ECG data 1102 to confirm that the library of ECG images 1115 are diagnostically equivalent to the raw data. That is diagnostically equivalent means that a trained clinician would give the same diagnosis for the patient health condition on viewing the diagnostically equivalent ECG as he would if viewing he raw ECG data. In one embodiment the diagnoses are done algorithmically using a plurality of algorithms as described in FIGS. 1-6. This is illustrated in the remainder of FIG. 11. An ECG 1107 is acquired from a patient 1106. The raw data may be stored 1108 for further analysis or to corroborate a diagnosis. The ECG data 1107 is matched 1109 against the stored library of ECG images 1104 and the best match is selected to produce the diagnostically equivalent ECG 1110. The diagnostically equivalent ECG is presented to a clinician 1111. The clinician may further confirm the diagnosis by observing the patient 1106 and take action on the basis of the diagnosis. The clinician may be remote from the patient. In such a case the data transmitted from the patient to the location of the clinician may be a tabular selection of the images from the ECG library 1104 rather than raw ECG data thereby reducing the amount of data and still maintaining the ability of the clinician to make the same diagnosis as if the full disclosure ECG were transmitted. As an example the full disclosure ECG data 1107 is typically acquired at 250 or more data points per second each data point representing 12 or more bits of data. Therefore, the full disclosure ECG may comprise of 1000 kilobytes of data for just 4 seconds of ECG. Where the diagnostically equivalent ECG may consist of a single byte corresponding to a numerical index of a selected ECG image from the library for each of the heartbeats observed in the acquired ECG. The amount of data to be transmitted may be reduced from 1000 kilobytes to just a few bytes while providing diagnostically equivalent data to the clinician. Reduction in the data transmission requirement of one to three or more orders of magnitude means that the continuous monitoring may be done at a lower cost with faster transmission and reduced requirements on the quality of the connection between a remote patient and a clinician. In another embodiment the clinician 1111 may confirm the diagnosis provided from the database by observation of the patient 1106 and the association of the diagnosis and the ECG images in the database may be used to update 1112 the database to further ensure the accuracy and completeness of the database. In one embodiment update 1112 includes addition of new images to the database 1104. In another embodiment the images 1115 are not images of a complete heartbeat but rather are images of individual peaks observed in the ECG data 1102. In one embodiment the individual peaks are used to create separate libraries of images for matching to each of the P, Q, R, S, T and U typically peaks observed in an ECG.

Figure 12:
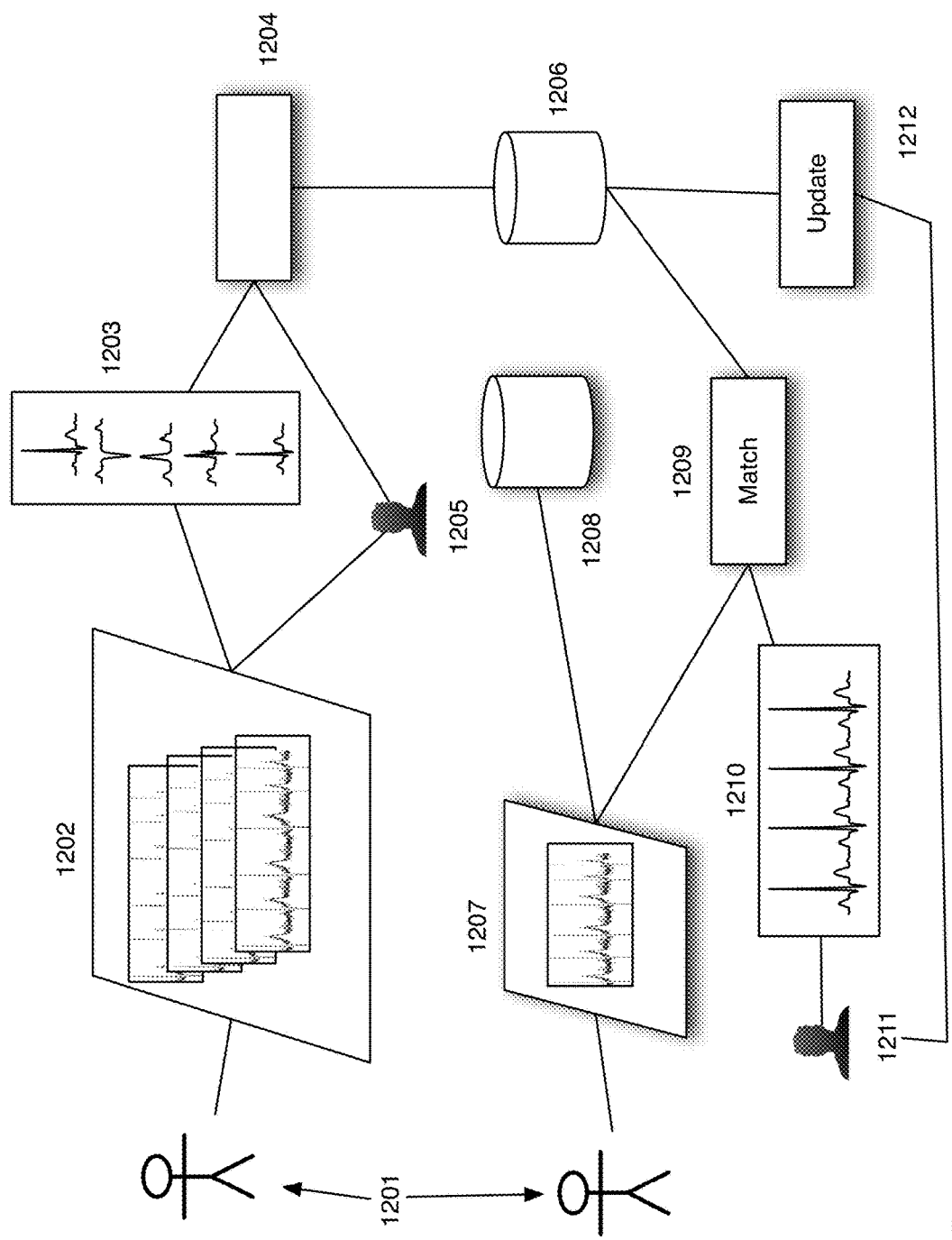
FIG. 12 is a flow chart showing construction of a clinically equivalent electrocardiogram from actual data where the template library is created from electrocardiogram data specific to the single patient.

In another embodiment shown in FIG. 12 the library of ECG images used to create the diagnostically equivalent ECG is created from the same patient who is being monitored. At a first point in time ECG data 1202 is acquired from a patient 120. The raw ECG data is filtered and otherwise processed through curve fitting to produce a library of ECG images 1203. In one embodiment the ECG images are of a complete heartbeat cycle. In another embodiment the ECG images are images of individual peaks observed in an ECG. In one embodiment the library is a set of libraries one each for P, Q, R, S, T and U peaks observed in an ECG. A clinician also assesses 1205 the ECG data and provides diagnoses associated with the ECG images. In another embodiment the assessment is done automatically through use of multiple algorithms as described in FIGS. 1-6. In another embodiment the assessment includes observation of the patient 1201 by the clinician to confirm the diagnoses. The library of images and the diagnoses are combined 1204 and stored into a database 1206. At a second point in time ECG data 1208 is acquired from the same patient 1201. The full disclosure ECG data may be stored 1208 for corroboration of results or re-analysis if required. The ECG data 1207 is matched 1209 to ECG images in the stored database 1206 of ECG images to provide a diagnostically equivalent ECG 1210. The diagnostically equivalent ECG data is transmitted to a clinician 1211 who is notified of automated diagnoses of issues and also can corroborate the diagnosis. The clinician can further update 1212 the database of ECG images and associated diagnoses 1206 for future use in monitoring the patient 1201.

SUMMARY

Devices and methods are described that provide improved diagnosis from the processing of physiological data. The methods include use of multiple algorithms and intelligently combing the results of multiple algorithms to provide a single optimized diagnostic result. The algorithms are adaptive and may be customized for particular data sets or for particular patients. Examples are shown with applications to electrocardiogram data, but the methods taught are applicable to many types of physiological data. The diagnostic procedures are combined with acquisition, filtering and curve fitting of the electronic physiological data to produce a library of images of physiological data. Once created the library of images is used in monitoring patients by matching the real time physiological data with images in the library thus providing a diagnostically equivalent physiological data file. The diagnostically equivalent data aids in faster diagnoses and reduces the data burden for transmitting physiological data from remote locations.

Those skilled in the art will appreciate that various adaptations and modifications of the preferred embodiments can be configured without departing from the scope and spirit of the invention. Therefore, it is to be understood that the invention may be practiced other than as specifically described herein, within the scope of the appended claims.

What is claimed is:

1. A method for the analysis of electrocardiogram data acquired from a patient that outputs a diagnosis of the patient's health, said method comprising:
   a) acquiring a first set of electrocardiogram data during a first time period, by fitting electrocardiogram sensors to the patient, the sensors connected to an analog to digital converter, and, the sensors acquiring a voltage signal from the patient that is digitized by the analog to digital converter and stored in computer readable memory, the digitized, stored signal is the first set of electrocardiogram data, and,
   b) analyzing the first set of electrocardiogram data with an arrhythmia algorithm having a plurality of input parameters,
   c) wherein the plurality of input parameters are varied and found to present a set of different health diagnoses when varied and the arrhythmia algorithm is applied to the first set of electrocardiogram data,
   d) comparing the set of different health diagnoses, with a true diagnosis of the patient's health during the first time period,
   e) selecting an updated set of the plurality of input parameters on the basis of being the set of input parameters wherein the health diagnosis produced by the algorithm when using the updated set of the plurality of input parameters most nearly matched the true diagnosis of the patient's health during the first time period, and,
   f) acquiring a second set of electrocardiogram data during a second time period, and,
   g) analyzing the second set of electrocardiogram data with the arrhythmia algorithm using the updated plurality of input parameters producing a diagnosis of the patient's health during the second time period, and,
   h) outputting the diagnosis of the patient's health during the second time period.

2. The method of claim 1 wherein comparing the set of different health diagnoses, with a true diagnosis of the patient's health during the first time period and the updated set of the plurality of input parameters are selected by a technician review, said technician located remote from the patient.

3. The method of claim 2 wherein the updated set of the plurality of input parameters are optimized for a subset of other patients where certain similarity of physiological data with the patient, is observed.

4. The method of claim 2 wherein reviewing the diagnosis results further includes data extrinsic to the electrocardiogram data in the technician review to select the updated set of the plurality of input parameters, wherein the extrinsic data is one selected from:
   a) recent medication of the patient, and,
   b) physical position of the patient, and,
   c) whether the patient is fit with a pacemaker.

5. The method of claim 1 wherein the plurality of input parameters include at least one selected from: a threshold alarm limit on the patient's heart rate, whether a P wave is detected in the first set of electrocardiogram data, values for the integrated area under the P wave in the first set of electrocardiogram data, and, number of consecutive heart beats to be included in the analysis.

6. The method of claim 5 wherein comparing the set of different health diagnoses, with a true diagnosis of the patient's health during the first time period and the updated set of the plurality of input parameters are selected by a technician review, said technician located remote from the patient.

7. The method of claim 5 wherein the updated set of the plurality of input parameters are optimized for a subset of other patients where certain similarity of physiological data is observed.

8. The method of claim 5 wherein reviewing the diagnosis results further includes data extrinsic to the electrocardiogram data in the technician review to select the updated set of the plurality of input parameters, wherein the extrinsic data is one selected from:
   a) recent medication of the patient, and,
   b) physical position of the patient, and,
   c) whether the patient is fit with a pacemaker.

* * * * *